US00PP35243P2

(12) United States Plant Patent
Dirr et al.

(10) Patent No.: US PP35,243 P2
(45) Date of Patent: Jul. 4, 2023

(54) ***LANTANA* PLANT NAMED 'PII-LC1'**

(50) Latin Name: *Lantana camara*
Varietal Denomination: PII-LC1

(71) Applicant: Premier Introductions Inc, Watkinsville, GA (US)

(72) Inventors: Michael Dirr, Watkinsville, GA (US); Jeff Beasley, Watkinsville, GA (US); Mark Griffith, Watkinsville, GA (US)

(73) Assignee: Premier Introductions Inc., Watkinsville, GA (US)

( * ) Notice: Subject to any disclaimer, the term of this patent is extended or adjusted under 35 U.S.C. 154(b) by 0 days.

(21) Appl. No.: 18/074,596

(22) Filed: Dec. 5, 2022

(51) Int. Cl.
*A01H 5/02* (2018.01)
*A01H 6/86* (2018.01)

(52) U.S. Cl.
USPC ..... Plt./227

(58) Field of Classification Search
USPC ..... Plt./227
CPC ..... A01H 5/02; A01H 5/00; A01H 6/86
See application file for complete search history.

*Primary Examiner* — June Hwu
(74) *Attorney, Agent, or Firm* — Cassandra Bright

(57) ABSTRACT

A new and distinct cultivar of *Lantana* plant named 'PII-LC1' is disclosed, characterized by a unique golden-orange flower color. Plants are hardy to USDA Zone 7. The new variety is a *Lantana*, typically produced as an outdoor ornamental plant.

1 Drawing Sheet

Latin name of the genus and species: *Lantana camara.*
Variety denomination: 'PII-LC1'.

BACKGROUND OF THE INVENTION

The new cultivar is a product of open pollination discovered by the inventors, at a commercial nursery in Watkinsville, Ga. The precise date of the open-pollination in unknown.

The seed parent is the variety *Lantana* 'Chapel Hill Yellow', U.S. Plant Pat. No. 19,548. The pollen parent cannot be identified as this new selection resulted from an open-pollination.

The new variety was found and selected by the inventors May 8, 2020, at the same nursery in Watkinsville, Ga.

Asexual reproduction of the new cultivar 'PII-LC1' was first performed Jul. 1, 2020 in Watkinsville, Ga., by vegetative cuttings. Through subsequent propagation, multiple additional generations have been reproduced, having shown that the unique features of this cultivar are stable and reproduced true to type.

SUMMARY OF THE INVENTION

The cultivar 'PII-LC1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'PII-LC1.' These characteristics in combination distinguish 'PII-LC1' as a new and distinct *Lantana* cultivar:

1. Unique golden-orange flower color.
2. Hardiness to USDA Zone 7.

PARENT COMPARISON

Plants of the new cultivar *Lantana* 'PII-LC1' can be compared to the seed parent variety *Lantana* 'Chapel Hill Yellow'. Plants of 'PII-LC1' are similar to plants of the seed parent in most horticultural characteristics, however, plants of 'PII-LC1' differ in the following:

1. Flowers of the new variety are a unique golden-orange color, while flowers of the seed parent are bright yellow.

COMMERCIAL COMPARISON

Plants of the new cultivar *Lantana* 'PII-LC1' can be compared to the commercial variety *Lantana* 'New Gold', unpatented. Plants of 'PII-LC1' are similar to plants of 'New Gold' in most horticultural characteristics, however, plants of 'PII-LC1' differ in the following:

1. The new variety is hardy to USDA zone 7, whereas 'New Gold' is hardy to USDA zone 10.

Plants of the new cultivar *Lantana* 'PII-LC1' can be compared to the commercial variety *Lantana* 'Luscious Goldengate', patent status unknown. Plants of 'PII-LC1' are similar to plants of 'Luscious Goldengate' in most horticultural characteristics, however, plants of 'PII-LC1' differ in the following:

1. The new variety is hardy to USDA zone 7, whereas 'Luscious Goldengate' is hardy to USDA zone 9.
2. Plants of the new variety grow wider than plants of 'Luscious Goldengate'.

BRIEF DESCRIPTION OF THE PHOTOGRAPH

The accompanying photograph illustrates in full color an inflorescence of 'PII-LC1'. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'PII-LC1' plants grown outdoors in Watkinsville, Ga. The plants were about 1 year old. Temperatures ranged from 12° C. to 15° C. at night to 18° C. to 27° C. during the day. No artificial light, photoperiodic treatments were given to the plants. Measurements and numerical values represent averages of typical plant types.

Botanical classification: *Lantana camara* 'PII-LC1'.

PROPAGATION

Time to initiate roots: About 5 to 6 days.

Root description: Fibrous and well branched. Colored near RHS Grey-Brown 199A, 199B, 199C and N199A, N199C.

PLANT

Age of plant described: Approximately 12 weeks from a rooted cutting.

Pot size of plant described: 1-gallon.

Growth habit: Semi-trailing to somewhat spreading.

Height: 16 cm.

Plant spread: 32 cm.

Growth rate: Moderate.

Branching characteristics: Well branched, basal and lateral branching.

Length of primary lateral branches: 10 to 15 cm.

Diameter of lateral branches: 3 to 4 mm.

Quantity of primary lateral branches: 4 to 6.

Characteristics of primary lateral branches:

- *Form*.—Round. Slightly ribbed longwise.
- *Color*.—New Growth: Near RHS Yellow-Green 144B. Mature growth: Slightly woody, RHS Grey-Brown 199A striated Greyed-Green 198A.
- *Texture*.—New growth hirsute, mature growth roughly striated.
- *Strength*.—Moderately strong, somewhat brittle.

Internode length: 2 to 3.5 cm.

FOLIAGE

Leaf:

- *Arrangement*.—Opposite.
- *Quantity*.—Approximately 24-36 per branch.
- *Average length*.—2.5 cm to 3.2 cm.
- *Average width*.—2.0 to 2.5 cm.
- *Shape of blade*.—Broadly ovate.
- *Apex*.—Acute.
- *Base*.—Rounded.
- *Margin*.—Denate.
- *Texture of top surface*.—Hirsute.
- *Texture of bottom surface*.—Hirsute. Less pubescent than the upper surface.
- *Aspect*.—Slight upward fold.
- *Color*.—Young foliage upper side: Near RHS Green 137A. Young foliage under side: Near RHS Green 138A. Mature foliage upper side: Near RHS Green 139A. Mature foliage under side: Near RHS Green 138A.
- *Venation*.—Midrib with secondary veins and very dense tertiary veins across. Venation color upper side: Near RHS Yellow-Green N144A. Venation color under side: Near RHS Yellow-Green 145A.

Petiole:

- *Length*.—8 mm.
- *Diameter*.—2 mm.
- *Color*.—Near RHS Yellow-Green N144B.
- *Texture*.—Sparsely and roughly pubescent.

FLOWER

Natural flowering season: Spring through Fall. Continuously producing new inflorescences.

Days to flowering from rooted cutting: About 8 weeks.

Inflorescence and flower type and habit: Umbel.

Individual flower shape: Trumpet shaped.

Rate of flower opening: 4 to 6 days from bud to fully opened flower.

Flower longevity on plant: 1 to 2 weeks (depending on outdoor temperature, higher temperatures result in shorter flower longevity).

Persistent or self-cleaning: Self-cleaning.

Overall inflorescence size:

- *Height*.—Approximately 2 cm.
- *Diameter*.—Approximately 3 cm.

Individual flower size:

- *Length*.—Approximately 1.5 cm.
- *Diameter*.—Average about 7 mm.

Bud:

- *Shape*.—Tubular.
- *Length*.—5 to 10 mm.
- *Diameter*.—4 to 6 mm.
- *Color*.—Tip near RHS Yellow-Orange 17A. Central section near Yellow 13B. Base near Yellow-Green 150C.

Corolla:

- *Petals/lobes*.—Number: 4 lobes fused together forming a radial shape. Length: Upper and lower lobes about 4 to 5 mm. Right and left lobes about 3 to 4 mm. Width: Upper and lower lobes about 4 to 5 mm. Right and left lobes about 3 to 4 mm.
- *Shape*.—Single, rounded. Aspect: Straight from the base of the inflorescence. Margin: Entire. Texture: Smooth.

Color:

- *When opening*.—Upper surface: Near RHS Yellow-Orange 21A. Lower surface: Near RHS Yellow-Orange 23B.
- *Fully opened*.—Upper surface: Near RHS Yellow-Orange 23B. Lower surface: Near RHS Yellow-Orange 17B.
- *Throat/tube*.—Color: Interior: Near RHS Yellow-Orange 16C and 16D. Exterior: Near RHS Yellow-Orange 16A and 16B. Base near Green-White 157A. Texture: Pubescent, covered with tiny dense smooth hair resembling silk.

Calyx/sepals:

- *Form*.—2 oblong bracts fuse together, forming a tubular shape.
- *Length*.—About 4 to 5 mm.
- *Diameter*.—About 2 to 3 mm.
- *Sepal shape*.—Strap shaped.
- *Sepal margin*.—Entire.
- *Sepal texture*.—Sparsely hirsute.
- *Sepal color*.—Near RHS Green 143C.

Flower bracts/inflorescence bracts:

- *Arrangement*.—Solitary, single occurring under each flower within the inflorescence.
- *Length*.—Approximately 3 mm.

*Width*.—Approximately 2 to 3 mm.
*Shape*.—Strap shaped.
*Apex*.—Sharply pointed.
*Margin*.—Entire.
*Texture*.—Sparsely pubescent.
*Color*.—Near RHS Green 143C, all surfaces.

Peduncles:
*Length*.—Approximately 1.5 to 3.0 cm.
*Diameter*.—Approximately 2 mm.
*Angle*.—About 45°.
*Strength*.—Strong.
*Texture*.—Very short hirsute.
*Color*.—Near RHS Green 143C.
*Flower fragrance*.—Earthy, musty.

REPRODUCTIVE ORGANS

Stamens:
*Number* (*per flower*).—4.
*Filament length*.—3 mm.
*Anthers*.—Shape: Linear. Length: 1 mm. Color: Near RHS Grey-Brown N199B.

Pollen: None.

Pistils:
*Quantity per flower*.—1.
*Length*.—2 to 3 mm.
*Color*.—Near Yellow 13D.
*Ovary color*.—Near RHS 143C.
*Stigma*.—Shape: Globular. Color: Near RHS Yellow 2C.

OTHER CHARACTERISTICS

Seeds and fruits: None.

Disease/pest resistance: Neither resistance nor susceptibility to common diseases and pests of *Lantana* has been observed.

Temperature tolerance: Hardy to USDA Zone 7. Observed to tolerate temperatures to 39° C. without negative effects.

What is claimed is:

1. A new and distinct cultivar of *Lantana* plant named 'PII-LC1' as herein illustrated and described.

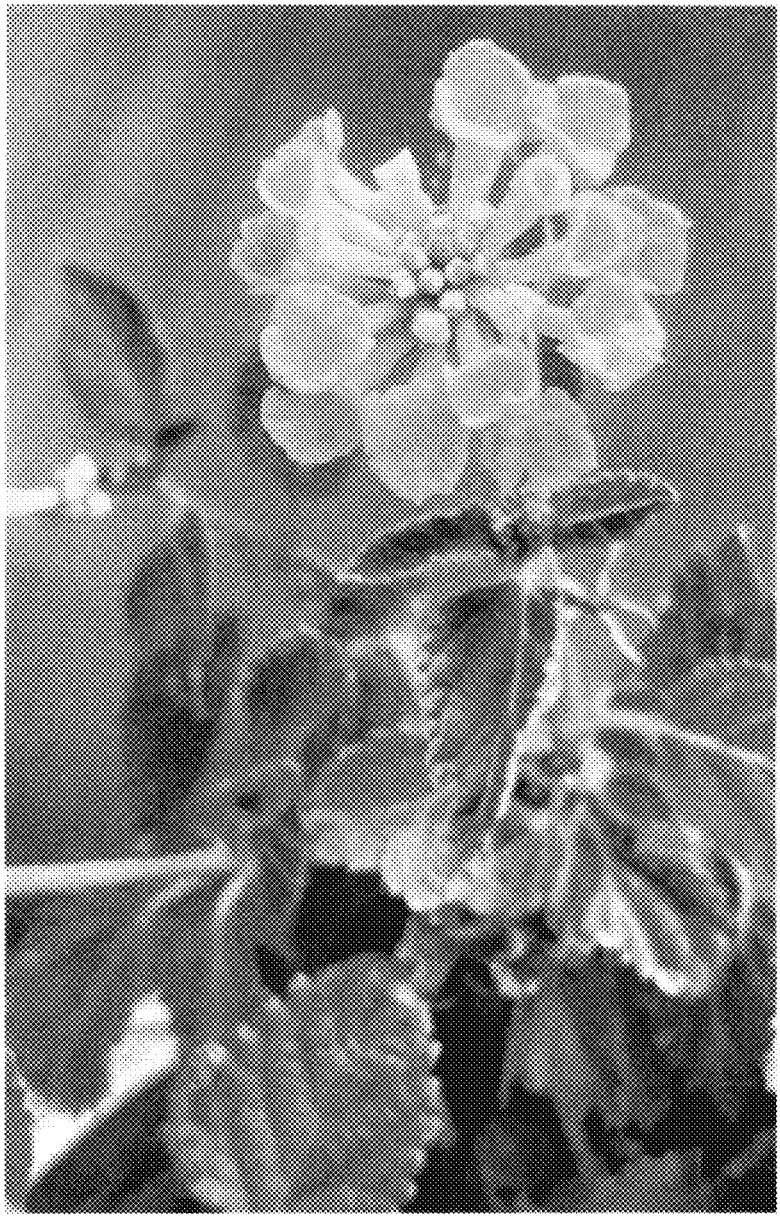

* * * * *